United States Patent [19]

Stewart, II

[11] Patent Number: 5,431,909

[45] Date of Patent: * Jul. 11, 1995

[54] STABILIZATION OF HUMAN INTERFERON

[75] Inventor: William E. Stewart, II, Lewisville, Tex.

[73] Assignee: Dallas Biotherapeutics, Inc., Dallas, Tex.

[*] Notice: The portion of the term of this patent subsequent to Aug. 17, 2010 has been disclaimed.

[21] Appl. No.: 105,923

[22] Filed: Aug. 13, 1993

Related U.S. Application Data

[63] Continuation-in-part of Ser. No. 790,670, Nov. 7, 1991, Pat. No. 5,236,707.

[51] Int. Cl.$^6$ .............................................. A61K 45/00
[52] U.S. Cl. .................................. 424/85.4; 424/85.7; 424/85.5; 424/85.6; 530/351
[58] Field of Search ............... 530/351, 357; 424/85.4, 424/85.7, 85.5, 85.6

[56] References Cited

U.S. PATENT DOCUMENTS

| | | |
|---|---|---|
| 3,981,991 | 9/1976 | Stewart et al. . |
| 4,017,600 | 4/1977 | Stewart et al. . |
| 4,462,985 | 7/1984 | Cummins, Jr. . |
| 4,462,986 | 7/1984 | Smith . |
| 4,496,537 | 1/1985 | Kwan . |
| 4,503,035 | 3/1985 | Pestka et al. . |
| 4,675,184 | 6/1987 | Hasegawa et al. . |
| 4,680,175 | 7/1987 | Estis et al. . |
| 4,957,734 | 9/1990 | Miller . |
| 5,165,921 | 11/1992 | Ganesh et al. . |
| 5,326,892 | 8/1993 | Stewart ............................ 424/85.7 |

FOREIGN PATENT DOCUMENTS 0077063 4/1983 European Pat. Off. .

OTHER PUBLICATIONS

Adolf et al., "Isolation and Characterization of Components of Human Leukocyte Interferon", Journal of Interferon Research, vol. 10 (suppl. 1), Nov. 1990, p. S57.
Stewart II, W. E., "The Interferon System", Springer-Verlag (2d Ed 1981), pp. 17–18.
Stewart II, W. E., "Distinct Molecular Species of Interferons", Virology 61, (1974), pp. 80–86.
Eron et al., "Interferon Therapy for Coindylomata Acuminata", The New England Journal of Medicine, vol. 315, No. 17, Oct. 23, 1986, pp. 1059–1064.
Gall et al., "Efficacy of Human Lymphoblastoid Interferon in the Therapy of Resistant Condyloma Acuminata", Obstetrics & Gynecology, vol. 67, No. 5, May 1986, pp. 643–651.
Stewart II, et al., "Stabilization of interferons by defensive reversible denaturation", Nature vol. 249, May 31, 1974, pp. 460–461.
Stewart II, et al., "Elimination of size and charge heterogeneities of human leukocyte interferons by chemical cleavage", Proc. Natl. Acad. Sci. USA, vol. 74, No. 10, Oct. 1977, pp. 4200–4204.
Stewart II, et al., "Effect of Glycosylation Inhibitors on the Production and Properties of Human Leukocyte Interferon", Virology 97, (1979), PP. 473–476.
The University of Chicago, "Intralesional Administration of Large Doses of Human Leukocyte Interferon for the Treatment of Condylomata Acuminata", The Journal of Infectious Diseases, vol. 150, No. 4, Oct. 1984, pp. 612–615.
Brzoska et al., B4–7, Phase II Clinical Trials of Interferon Beta Gel (Fiblaferon–Gel) in Dermatological Diseases, p. 5259.

(List continued on next page.)

Primary Examiner—Howard E. Schain
Assistant Examiner—P. Lynn Touzeau
Attorney, Agent, or Firm—Baker & Botts

[57] ABSTRACT

The invention relates to methods for stabilizing human interferon, including pharmaceutical compositions useful in topical applications for the treatment of disorders such as *Condyloma acuminata*. Amine stabilizing agents such as primary aliphatic amines and anionic stabilizing agents such as lithium organo sulfates protect human interferons from degradation and provide enhanced storage stability. These stabilizing agents containing interferon can be added to appropriate pharmaceutical carriers for topical applications. The topical products also exhibit enhanced storage stability.

40 Claims, 2 Drawing Sheets

OTHER PUBLICATIONS

Vesterinen, et al., "Topical Treatment of Flat Vaginal Condyloma With Human Leukocyte Interferon", Obstetrics & Gynecology, vol. 64, No. 4, Oct. 1984, pp. 535–538.

Kesy et al., "Topical Interferon for Treating Condyloma Acuminata in Women", The Journal of Infectious Diseases, vol. 158, No. 5, Nov. 1988, pp. 934–939.

Vesterinen et al., "Treatment of Vaginal Flat Condyloma with Interferon Cream", The Lancet, Jan. 21, 1984 p. 157.

Marcovici et al., "Human fibroblast Interferon Therapy in Patients With Condyloma Accuminata" p. 104.

Ikic et al., "Therapeutical Effect of Human Leukocyte Interferon Incorporated Into Ointment and Cream on Condylomata Acuminata", Proc. Symposium on Clinical use of Interferon, 1975, pp. 235–238.

Smiles et al., "Activity of Intralesional Interferon ALFA–2B in Viral and Malignant Skin Diseases", The Biology of Interferon System, pp. 493–501, 1986.

Friedman–Kien et al., "Natural Interferon Alfa for Treatment of Condylomata Acuminata", JAMA, Jan. 22/29, 1988, vol. 259, No. 4, pp. 533–538.

IKIC et al., "Preliminary Study of the Effect of Human Leukocytic Interferon on Condylomata Acuminata in Women" Proc. Symposium on Clinical Use of Interferon, 1975, pp. 223–227.

IKIC et al., "Double Blind Clinical Study With Human Leukocyte Interferon in the Therapy of Condylomata Acuminata", Proc. Symposium on Clinical Use of Interferon, 1975, pp. 229–233.

FIG.IA
1. NON-OXYNOL-9

2. POLYOXYETHYLENE (Brij & Tween Series)

3. TRITON-X-100

FIG.IB
1. CETYL PYRIDINIUM CHLORIDE

2. BENZALKONIUM CHLORIDE

FIG.IC
1. LITHIUM DODECYL SULFATE

2. DODECYL ARMINE CHLORIDE

STABILIZATION OF HUMAN INTERFERON

CROSS-REFERENCE TO RELATED APPLICATION

This is a continuation-in-part application of U.S. Ser. No. 07/790,670, filed Nov. 7, 1991, now U.S. Pat. No. 5,236,707.

BACKGROUND

1. Field of the Invention

This invention relates to methods for stabilizing human interferon and to compositions of stabilized human interferon for use as pharmaceuticals. Stabilized interferon compositions comprise alpha interferon, omega interferon or mixtures thereof, and stabilizing agents. The invention also relates to medical dressings for delivering stable interferon to affected areas of the body.

2. Description of the Background

Interferons are proteins having a variety of biological actions including antiviral, immunomodulating and antiproliferative effects. Cellular production of interferons may be stimulated by numerous agents, including viruses. Interferons protect animal tissues and cells against viral attack and are an important host defense mechanism. Interferon may be produced endogenously by numerous cell types such as leukocytes, fibroblasts and lymphocytes, and may also be produced in cell culture or recombinantly. In most cases, interferons provide better protection to tissues and cells of the kind from which they have been produced than to other types of tissues and cells, indicating that human-derived interferon should be more efficacious in treating human diseases than interferons from other species. There are several distinct types of interferons, generally classified as alpha, beta, gamma and omega interferons, and a large number of variants thereof.

The alpha and omega interferons are derived primarily from leukocytes. Cell-derived interferon such as leukocyte interferon is difficult to purify to homogeneity and, as a consequence, is most often used as a crude or partially purified preparation. Leukocyte interferon preparations contain two molecular populations (alpha and omega interferons) that are distinguishable physically, chemically and biologically. Alpha interferon comprises approximately 80% of leukocyte interferon activity, and omega interferon comprises about 20% of leukocyte interferon activity. The leukocyte interferon forms can be separated by sodium dodecyl sulfate—polyacrylamide gel electrophoresis (SDS-PAGE) into slow- and fast-migrating components as described by W. E. Stewart II and J. Desmyter (J. Virol. 67:68–73, 1975). The larger leukocyte interferon forms have apparent molecular weights of about 21,000–25,000 Daltons, while the smaller leukocyte interferon forms have apparent molecular weights of about 15,000–18,000 Daltons. The larger (omega) interferon are glycosylated, whereas the smaller (alpha) interferon are not. General discussions of these and other interferons can be found in various texts and monographs including: *The Interferon System* (W. E. Stewart, II, Springer-Verlag, N.Y. 1979); and *Interferon Therapy* (World Health Organization Technical Reports Series 676, World Health Organization, Geneva 1982). The method of administering interferon is an important factor in the clinical application of this important therapeutic agent. Systemic administration of interferon by either intravenous, intramuscular or subcutaneous injection has been most frequently used with some success in treating disorders such as hairy cell leukemia and Acquired Immune Deficiency Syndrome (AIDS)—related Kaposi's sarcoma. Among the problems inherent in intravenous, intramuscular or subcutaneous administration is that interferon can come into contact with uninfected or nonmalignant cells, and may thereby cause unwanted side effects such as fever, malaise and myalgia.

Condyloma acuminata (genital warts), a widespread, sexually transmitted disease of major public health concern, is a benign condition caused by human papilloma viruses (HPV). The Centers for Disease Control reported that the incidence of condyloma acuminata in the United States was at 160,000 in 1966, 1,400,000 in 1986, and over 3,000,000 in 1991. If this logarithmic growth continues, the number of infected patients is expected to reach about ten million by the year 2000.

In a recent study, HPV has also been shown to be the cause a number of cervical malignancies (F. X. Bosch et al., Second International Workshop on the Epidemiology of Cervical Cancer and Human Papilloma Virus. Int. J. Cancer 52:171–73, 1992). During the 16 years from 1974 through 1989, there have been more than a dozen studies published on the efficacy of topical applications of interferon for the treatment of condyloma acuminata (D. Ikic et al., Third Annual International Congress for Interferon research, Miami, Fla. 1982). These studies all utilized fleshly prepared batches of interferon ointment which were directly applied to the afflicted areas. Collectively, these studies resulted in a cure for 57% of those patients treated.

In some cases it would be preferable to administer interferon directly to the affected tissues or organs. This may be accomplished by direct injection of interferon into the diseased site such as done in selected cases of condylomata acuminata (genital warts), involving the external surfaces of genital or perianal areas. Interferon can also be administered by local topical application directly to the diseased site, such as a viral-induced skin lesion. Topical interferon may be useful for treatment of conditions such as condylomata acuminata, cervical dysplasia, rectal cancer, basal cell carcinoma, penile cancer or any other disorder responsive to interferon, particularly those linked to papilloma virus infection. Topical application in these cases could reduce the unwanted side effects associated with intramuscular, intravenous or subcutaneous administration. Also, the patient could self-administer topical interferon without the direct assistance of a qualified health-care worker. A topical interferon product could also promote patient compliance by providing a more pleasant therapeutic experience for the patient than interferon treatment via injection.

The lack of interferon stability in solutions and other products has heretofore limited its utility. Interferon products having enhanced storage stability should facilitate more wide-spread use of this important therapeutic agent. Several factors are important in designing a useful topical interferon preparation. First, conventional topical interferon preparations are generally considered unstable, and therefore are considered to have a limited shelf-life. A topical interferon preparation should be stabilized to prevent degradation over time and upon shipping and handling. Second, because interferon generally has a higher molecular weight than the molecular weights of the therapeutic agents usually administered in topical preparations, interferon should be incorporated into a substance which sufficiently holds the high molecular weight interferon in suspension during packaging, shipping and application, and yet also be able to release the substance from the preparation in a reasonable length of time once it has been applied to the diseased site. Third, the preparation must not adversely affect the antiviral activity of interferon.

Interferon has a well documented instability in ointment formulations. In one study, interferon-alpha ointment lost 80% of its activity in a period of two weeks at 4° C. (Moller et al., Third Annual International Congress for Interferon research, Miami, Fla. 1982). In another study, a similar ointment lost 50% of its activity during this same time period when tested at room temperature and lost 50% of its activity (even when it contained the nonionic and cationic agents of Asculai and Miller, i.e., Tween-80 and Benzalkonium-Chloride (L. F. Estis et al., U.S. Pat. No. 4,680,175) by six hours at 37° C. In studies performed by myself, preparations of interferon-alpha ointment lost 30% of their activity after one month at 4° C., and 100% of its activity after one month at room temperature.

Figure 1A:
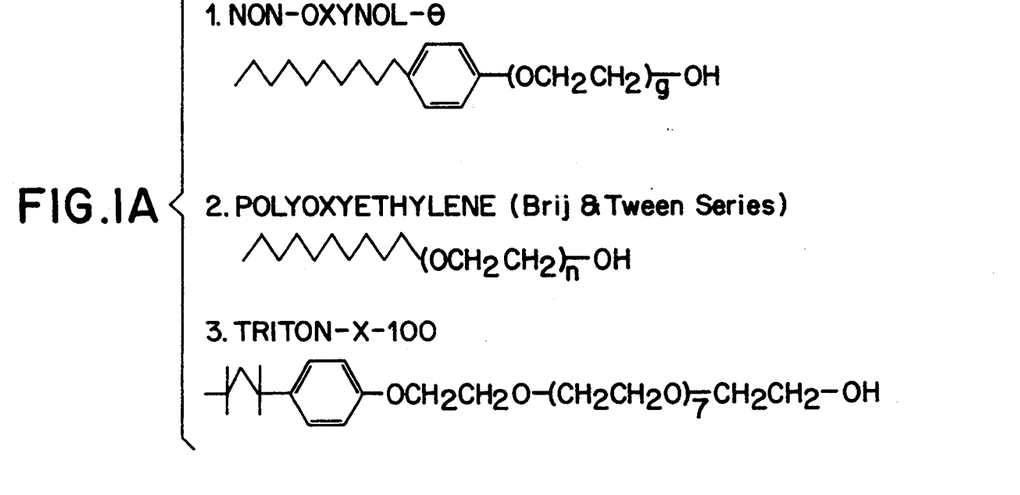
Figure 1B:
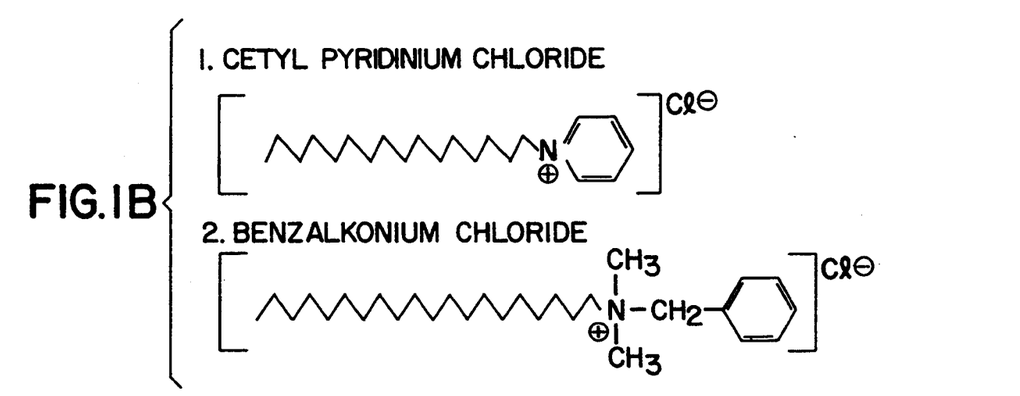
Figure 1C:
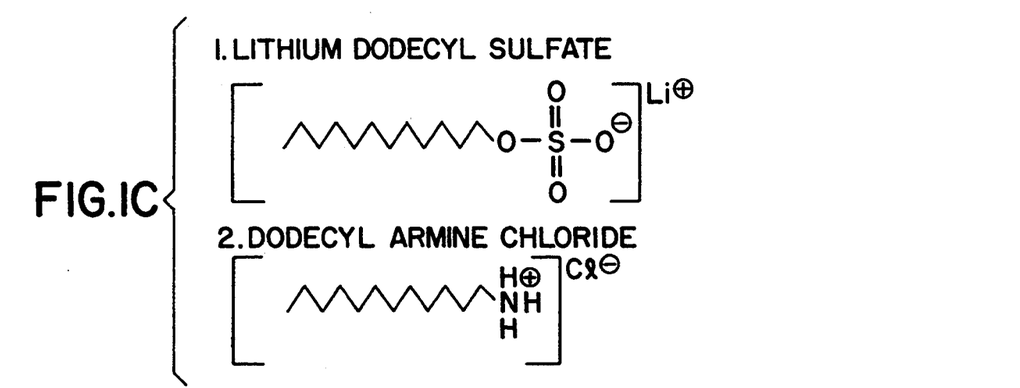
Figure 2A:
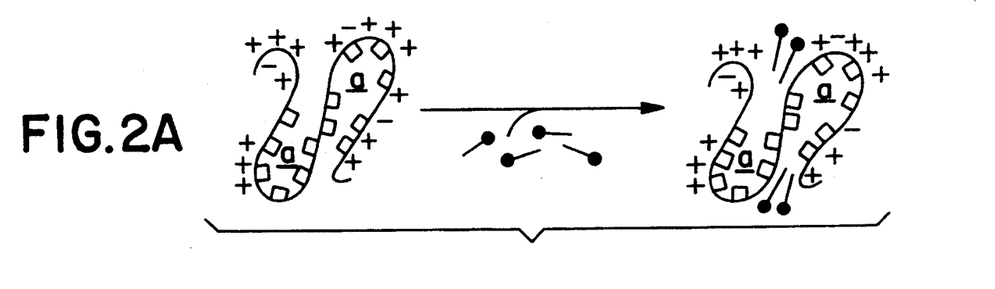
Figure 2B:
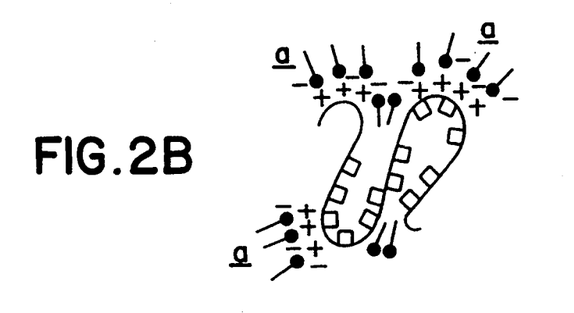
Figure 2C:
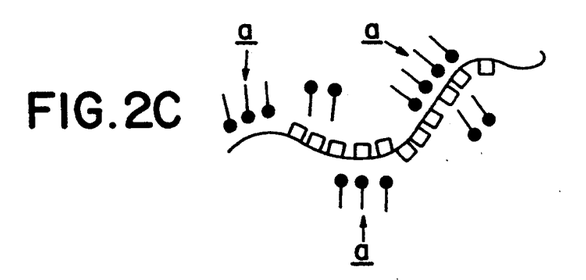
Figure 2D:
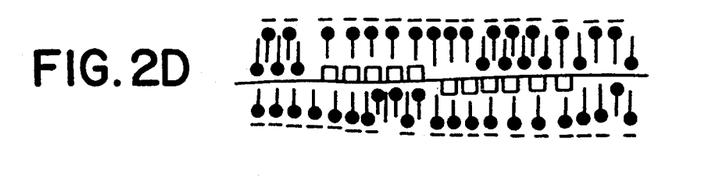

Asculai (European Patent Application No. 0077063) and Miller (U.S. Pat. No. 4,957,734), are directed to pharmaceutical compositions containing antiviral surface active agents. The compounds specifically referred to by these inventors are the nonionic surface active agents, such as non-oxynol-9, Brij, and Triton-X-100 (FIG. 1-A), the anionic surface active agents, sodium alkyl sulfonate and sodium alkyl benzene sulfonate, and two cationic surface active agents, the quaternary amine detergents, cetyl pyridinium chloride and benzalkonium chloride (FIG. 1-B). None of these compounds are individually useful for the stabilization of interferon. Further, Miller uses nonionic, anionic and cationic surface active agents in combination with interferon, but claims no stabilization of interferon and discloses that quaternary ammonium detergents such as cetyl pyridinium chloride and benzalkonium chloride are preferable cationic agents.

Nonionic surface active agents do not stabilize interferon and other similar proteins (K. Hasegawa et al., U.S. Pat. No. 4,675,184; L. F. Estis U.S. Pat. No. 4,680,175). Estis et al. is directed to the use of protease inhibitors such as alpha-1-antitrypsin inhibitor, alpha-2 macroglobulin, soybean inhibitor, N-alpha-tosyl-L-lysine chloromethyl ketone, phenylmethylsulfonyl fluoride, and N-alpha-tosylphenylalanine chloromethyl ketone to stabilize topical interferon preparations. Hasegawa et al. is directed to anionic surface active agents such as sodium alkyl sulfates stabilize betainterferon (fibroblast-derived).

Stewart et al. (U.S. Pat. No. 3,981,991) is directed to interferon that can be stabilized by treating the antiviral agent with a combination of: 1) guanidine-hydrochloride or urea; 2) mercaptoethanol or ethanethiol; and 3) an agent selected from the group consisting of sodium dodecylsulfate, sodium decylsulfate, sodium dodecylsulfonate, dodecylamine and decylamine. Stewart et al. caution that interferon cannot be stabilized with only one or two of the aforesaid three agents.

SUMMARY OF THE INVENTION

This invention is directed to methods for stabilizing human interferon and to the resulting stabilized interferon. Human alpha or omega interferon, or mixtures thereof, can be stabilized when placed in solutions containing amines, and more particularly, primary aliphatic amines having from between 8 to 14 carbon atoms, and lithium salts of anionic stabilizing agents such as lithium organo sulfates. Stabilized interferon may be placed in a pharmaceutically acceptable carrier for topical administration. Further stability is achieved by adding additional amine-stabilizing agents to the stabilized interferon product.

One embodiment of the invention is directed to a method for making a composition of stabilized interferon comprising the steps of obtaining an amount of an interferon which is an alpha interferon, an omega interferon, or a combination thereof, mixing the interferon with an effective amount of a stabilizing agent which is a primary alkyl amine to form a composition, dialyzing the composition, and, optionally, lyophilizing the composition to a powder and mixing the powder with a pharmaceutically acceptable carrier to form a stabilized interferon composition.

Another embodiment of the invention is directed to a method for making a composition of stabilized interferon comprising the steps of obtaining an amount of an interferon which is an alpha interferon, an omega interferon, or a combination thereof, mixing the interferon with an effective amount of a stabilizing agent which has a formula $Li_nRX$ to from a composition, dialyzing the composition, and, optionally, lyophilizing the composition to a powder and mixing the powder with a pharmaceutically acceptable carrier to form a stabilized interferon composition.

Another embodiment of the invention is directed to compositions of stabilized interferon wherein stabilization is achieved by the addition of a stabilizing agent which is a primary alkyl amine or a chemical which has the formula $Li_nRX$.

Another embodiment of the invention is directed to methods and compositions comprising interferon and an other protein which acts synergistically with interferon. These compositions contain, for example, interferon and tumor necrosis factor or alpha interferon and gamma interferon. The proteins of these compositions are stabilized as described herein.

Another embodiment of the invention is directed to medical dressings comprised of stabilized interferon compositions which are incorporated onto a solid support. The interferon is stabilized as described herein and fixed to a solid support. The solid support is attached to a dressing such as a bandage and applied directly to the skin or other affected areas of the body. The interferon, being stable, treats the affected area over a period of time with minimal discomfort to the patient and without the need for continued reapplication.

Other advantages of the invention are set forth in part in the description which follows, and in part, will be obvious from this description, or may be learned from the practice of this invention. The accompanying drawings which are incorporated in and constitute a part of this specification, illustrate and, together with this description, serve to explain the principle of the invention.

DESCRIPTION OF THE DRAWINGS

FIG. 1 (A) Non-ionic detergents which dissolve the lipid membrane and do not denature the proteins; (B) Weak cationic detergents which dissolve the lipid membrane and do not denature the proteins; and (C) Strong ionic detergents which dissolve the lipid membranes and denature the protein.

FIG. 2 Step-wise depiction of the interaction between detergents and proteins during denaturation (Step 1) hydrophobic interactions; (Step 2) ionic binding of terminally-charged detergents; (Step 3) cooperative unfolding; and (Step 4) saturation binding with both hydrophobic and ionic interactions of the detergents and the polypeptide chain ("a"=hydrophobic areas).

DESCRIPTION OF THE INVENTION

The present invention overcomes the problems and disadvantages associated with current strategies and designs and provides a new method for stabilizing interferon to enhance its storage stability. This invention is applicable to all types of interferon including natural interferon, interferon produced by recombinant DNA technology, and interferon produced by chemical synthesis or modification. Also, the invention can be used with crude, semi-purified and purified interferon from leukocytes, fibroblasts, lymphocytes or any other interferon-containing or producing tissues from humans or any other appropriate species.

A method for producing interferon from leukocytes (comprising alpha interferon and omega interferon) is described by Cantell et al. (Methods in Enzymology, 78: 29-38, 1981). In general, the interferon produced by this method and other methods is supplied as a liquid. Alpha isolates and omega isolates of interferon are prepared by subjecting leukocyte interferon to non-reducing sodium dodecyl sulfate—polyacrylamide gel electrophoresis (SDS-PAGE) as described in W. E. Stewart II et al. (Proc. Natl. Acad. Sci. USA 74:4200–4204, 1977). Briefly, leukocyte interferon samples in 0.01M sodium phosphate buffer were constituted to contain 5M urea and 1% sodium dodecyl sulfate. Bromphenol blue in sucrose was added to make the samples 6% sucrose, and the samples were heated to 100° C. for one minute. Aliquots of 0.1 ml of sample were electrophoresed on parallel SDS-PAGE gels. When the dye front had migrated about 18 centimeters into gels, gels were sliced into 2.2 millimeter segments, and two adjacent slices were pooled into each fraction containing the alpha isolates and omega isolates, and were eluted overnight at 4° C. into 1 ml of Eagle's minimal essential medium containing 10% fetal calf serum.

The amount of interferon which is administered in any particular case, as well as the frequency at which the interferon is administered, depends upon such factors as the type of interferon used, the disease being treated, the patient's response to interferon treatment, and whether the preparation used is a semi-solid or a liquid. The National Institutes of Health (United States Department of Health and Human Services, Bethesda, Md.) have established unit strengths for interferon activity. In terms of these unit strengths, dosage levels for topical pharmaceutical preparations using crude or partially purified natural interferons can range from about 10,000 IU/gram of topical preparation to 1,000,000 IU/gram of topical preparation. Highly purified preparation of $10^6$ to $10^8$ IU/gram are preferable for certain formulation such as formulations for ocular application.

The term "stabilized interferon composition" is employed herein to describe an agent having an interferon and an amine stabilizing agent present in an effective amount to stabilize interferon. The interferon can be human interferon or interferon from any other appropriate species. Preferably the interferon is human leukocyte-derived interferon comprising alpha interferon, omega interferon or mixtures thereof. The interferon can also be recombinant interferon or interferon produced or modified chemically. The present invention reveals enhanced storage stability and antiviral activity of stabilizing agents for interferon.

The term "amine stabilizing agent" is employed herein to include primary, secondary, or tertiary amines. Preferably, the amine stabilizing agent is a primary amine having the general formula $RNH_2$ where "R" is an aliphatic group. Preferably, amine stabilizing agents have aliphatic groups of from about 8 to about 14 carbon atoms, although aliphatic groups having less than 8 or more than 14 carbon atoms are encompassed within the scope of this invention. More preferably, aliphatic primary amines having from between about 8 to about 14 carbon atoms may be used as amine stabilizing agents. Most preferably, the amine stabilizing agent is a primary aliphatic amine having an aliphatic group consisting of 12 carbon atoms. The aliphatic groups may be linear or branched, but are preferably linear. Representative examples of amines useful as amine stabilizing agents include octyl amine, decyl amine, dodecyl amine, and tetradecyl amine. Amine stabilizing agents having more than 14 carbon atoms are generally insoluble. Amine stabilizing agents having less than 8 carbon atoms are generally inefficient stabilizers. Most preferable of the amine stabilizing agents is dodecyl amine.

The concentrations of amine stabilizing agents may range from about 0.1% to about 10.0% by weight, although lower or higher concentrations may be used as would be ascertainable by a person having ordinary skill in the art. The effective amount of amine stabilizing agents to stabilize interferon in certain formulations, depending on the degree of purification of the interferon, can be less than about 0.1% and is preferably between about 0.0001% to 0.01% final detergent concentration. For example, such low concentrations have potential utilities such as topical applications for viral infections of the eye. Formulations containing 0.1% to 10% detergent, one to ten thousand times more concentrated, could be toxic if applied to the eyes. Compositions with these lower concentrations of stabilizing agents are still stable and useful against recurrent conjunctival papillomatosis, ocular herpes keratitis and other viral infections of the eye.

The term "lithium stabilized interferon composition" is employed herein to describe an agent having an interferon and a lithium anionic stabilizing agent present in an effective amount to stabilize interferon. The interferon can be human interferon or interferon from any other appropriate species. Preferably the interferon is human leukocyte-derived interferon containing alpha interferon or omega interferon or mixtures thereof. The interferon can also be recombinant interferon or interferon produced or modified chemically.

The term "lithium anionic stabilizing agent" is employed herein to include the lithium salts of compounds having a net negative charge. Lithium anionic stabilizing agents useful in this invention are lithium organo sulfates, and may be represented by the general formula "$Li_nRX$" where "R" is an aliphatic group, "X" is an anion and "n" is chosen to electrochemically balance the anion which is preferably sulfate. Lithium anionic stabilizing agents containing aliphatic groups having from about 8 to about 22 carbon atoms may be used, although aliphatic groups of more than 22 carbons or less than 8 carbons are encompassed within the scope of the present invention. Preferably, lithium anionic stabilizing agents contain 8 to 14 carbon atoms, and most preferably 12 carbon atoms. Representative examples of lithium anionic stabilizing agents include lithium octyl sulfate, lithium decyl sulfate, lithium dodecyl sulfate and lithium tetradecyl sulfate. The patent of Hasegawa et al., described above, does not disclose the use of lithium organo sulfate interferon stabilizers. As noted below, lithium-containing stabilizing agents have a clinical utility, as well as physio-chemical and physiological advantages, not possessed by sodium-containing stabilizing agents.

The concentrations of lithium anionic stabilizing agents may range from about 0.1% to about 10.0% by weight, although lower or higher concentrations may be used as would be ascertainable by a person having ordinary skill in the art. As above, in certain formulations, an effective amount of lithium stabilizing agent may be less than about 0.1% and preferably is between about 0.0001% and 0.01% final detergent concentration (depending on the purity of the interferon employed). Interferon compositions containing from about $1 \times 10^4$ to $1 \times 10^6$ IU/ml are preferably used in the present invention, although interferon compositions having lower or higher activity may also be used as would be readily ascertainable by a person having ordinary skill in the art including concentrations of about $10^6$ to about $10^8$ IU/ml.

The precise mechanism of action of the amine stabilizing agents and lithium anionic stabilizing agents in stabilizing interferon is not known, but is thought to be related to "defensive reversible denaturation" as described by W. E. Stewart II et al. (Nature 249:460–61, 1974) and W. E. Stewart II et al. (Preparative Biochemistry 4:383–93, 1974). This process predicts that certain charged surfactants, under the proper conditions, can bind to and denature proteins. Following this process, denatured proteins can be renatured by removal of the surfactant without significant loss in activity. An ionic surfactant is composed of a charged head group and an uncharged tail portion (FIG. 1-C). Ionic surfactants can interact with a protein at either its hydrophilic region or its hydrophobic region (FIG. 2). The head portion interacts with the charged, hydrophilic regions of the protein and the uncharged tail with the hydrophobic regions in any conformation (FIG. 2, step 1). However, with strongly charged cationic and anionic surfactants, the charged head groups can bind to oppositely charged side chains of the amino acids with the uncharged tails facing outward into the medium (FIG. 2, step 2). Similarly, the uncharged tails can bind directly to the hydrophobic portions with the charged head groups pointed outward directly into the medium (J. A. Reynolds and C. Tanford, Proc. Natl. Acad. Sci. USA 66:1002–07, 1970). This type of interaction fosters a cooperative unfolding of the protein which permits even more surfactants to bind (FIG. 2, step 3). When saturating amounts of surfactants bind to the protein a protective shell is formed which favors hydrogen bonding between tail portions (FIG. 2, step 4). Proteins encased in this manner have an overall net external positive or negative charge and are completely stabilized.

When encased proteins come into contact with proteins not so encased, such as those found in skin, hydrogen binding is no longer favored and is disrupted. This disruption allows for the simultaneous disconnection of the bound surfactants from the protein and renaturation of the protein's natural conformation without significant loss of activity. In contrast, nonionic surfactants have no charged head groups. Binding occurs with hydrophobic areas of the protein wherein the protein's original conformation is maintained. There is no cooperative unfolding and thus, no stabilization. However, the ability to interact in this manner does not effect the lipid dissolving process and thus, nonionic surfactants would still be useful as antiviral agents against enveloped viruses but would not be useful as antiviral agents against nonenveloped viruses (T. A. Armstrong and E. T. Froelich, Appl. Microbiol. 12:132–37, 1964).

The substitution of lithium for sodium in a stabilizing agent produces substantially different results because the two elements have substantially different physical and biological properties, particularly in regard to transmembrane ion pumps and ion channels. When compared to sodium, lithium has reduced toxicity in an interferon composition. For example, many sodium containing agents can cause chronic irritant dermatitis, from induced sodium ion transport and channeling, resulting in transdermal water loss and alteration of the protective properties of the skin. The anionic detergent, sodium dodecyl sulfate (SDS) is the most notorious in this regard, and some individuals, particularly infants, develop severe contact dermatitis when exposed to SDS residues in laundered undergarments (J. Priborsky et al., Toxicol. 70:344–46, 1992). Lithium forms of these compound do not have this problem.

Lithium compounds also have a large temperature range of solubility (Merck Index, Eleventh Ed., Merck & Co., 1989). Detergents can only act at temperature ranges higher than their critical micelle temperature, the temperature at which detergent crystals dissolve to form micelles and monomers in solution (A. Neugebauer, Calbiochem Monograph Series, 1992). Thus, a solution of sodium alkyl sulfate must be stored at or above room temperature to prevent crystallization. Lithium alkyl sulfate detergents of the claimed invention, however, remain in solution even at temperatures from between about 0° C. to 4° C. and thus, can be used in refrigerated environments, typically necessary for the long term storage of proteins. Also, colder storage temperatures reduce the potential of microbial contamination during the production and manufacturing processes.

Quaternary amine detergents, such as cetyl pyridinium chloride and benzalkonium chloride, also cannot effectively form ionic bonds with protein and thus, cannot stabilize proteins like interferon due to stearic hinderance. These compounds possess hydrophobic aromatic rings on the terminal ends which internalize and weaken the ionic characteristic of the molecule (FIG. 1-B). Absent a terminal ionic charge, these molecules are not or, at best, are only weakly, attracted to the opposite charges on the protein. Furthermore, hydrophobic aromatic rings occupy a significant amount of space which hinders ionic binding to the protein. Thus, large numbers of quaternary amine surfactants will not bind to the protein, no cooperative unfolding and no stabilization of interferon occurs (FIG. 2, steps 2–4).

The clinical utility of sodium-containing interferon stabilizing agents such as sodium organo sulfates is limited by the side effects associated with topical administration of sodium-salt-containing products. The substitution of lithium for sodium makes the properties of detergents distinctly different, principally by alter the activities and utilities. For example, only the sodium form induces chronic irritant dermatitis because sodium induces water loss by altering the skin barrier (F. Bettley, Brit. J. dermatol. 77:98, 1965). Transport across the skin is dependent on sodium-induced ion-transport by cell membranes. Increased sodium concentrations lead to instability and osmotic imbalances. Consequently, a not uncommon unwanted side effect associated with use of sodium-salt-containing products is chronic irritant dermatitis (R. A. Tupker et al., Acta Derm. Venereol. 70:1-5, 1990; J. Priborsky et al., Pharmacol. Toxicol. 70:344, 1992).

Further, ion-channel mediated movement of ions into and out of cells is also highly ion-selective, allowing the conduction of only one kind of ion present in physiological solution. Lithium ions are the least able to transport across cell membranes of any of the monovalent ions, and accordingly are the least likely to disrupt osmotic balance and cell volumes, whereas even minute increases in extracellular sodium ion concentrations drive the transport of this ion into cells, leading to toxic osmotic imbalances. (B. Pressman, Ann. Rev. Biochem. 45:501, 1976; D. Wilson, Ann. Rev. Biochem. 47:933, 1978; K. Sweadner and S. Goldin, New Engl. J. Med. 302:777, 1980; C. Stevens, Science 225:1346, 1984; L. Heginbotham et al., Science 258:1152, 1992). Thus, substitution of the lithium for the sodium in the anionic detergent-containing interferon formulations clearly offers the distinct physiological property of a product with less toxicity than is associated with topical application.

Additionally, lithium compounds are unique in their large temperature range of solubility in liquid phase and their solubility at low temperatures (0° C.–4° C.) are distinct physical-chemical properties that are advantageous for pharmaceutical products. Thus, while sodium dodecyl sulfate is insoluble at 4° C., and crystallizes out of solution lithium dodecyl sulfate remains soluble in solutions at 0° to 4° C. This physical-chemical property facilitates processing and storage of lithium-containing pharmaceutical products in the cold, with the advantages of impeding any potential chemical or enzymatic activity, or biological-contaminant growth that could adversely effect the product during processing and storage (C. Hemple, Encyclopedia of Chemical Elements, p. 374, 1968; ICN catalog p. 1036, 1992). A lithium-salt-containing interferon product would therefore represent an advance over sodium-salt-containing topical interferon preparations.

The term "interferon antiviral preparation" as used herein describes a product having a stabilized interferon composition and a pharmaceutically acceptable carrier, said pharmaceutically acceptable carrier itself containing substantially little or no amine stabilizing agent in the absence of the stabilized interferon composition. Effective amounts of amine stabilizing agent for stabilizing interferon in an interferon antiviral preparation are achieved when the weight of amine stabilizing agent exceeds the weight of total protein. Total protein may be determined by conventional techniques generally known to those skilled in the art. For example, total protein may be determined by the Lowry method or modifications thereof. Effective amounts of amine stabilizing agent (gram amine stabilizing agent per gram total protein) range from about 1.0 to about 10.0, and are most preferably about 1.44.

The term "lithium stabilized interferon antiviral preparation" as used herein describes a product having a lithium stabilized interferon composition and a pharmaceutically acceptable carrier, said pharmaceutically acceptable carrier itself containing substantially little or no lithium anionic stabilizing agent in the absence of the lithium stabilized interferon composition. Effective amounts of lithium stabilizing agent for stabilizing interferon in a lithium stabilized interferon antiviral preparation are achieved when the weight of lithium stabilizing agent exceeds the weight of total protein. Total protein may be determined by conventional techniques generally known to those skilled in the art. For example, total protein may be determined by the Lowry method or modifications thereof. Effective amounts of lithium stabilizing agent (gram lithium stabilizing agent per gram total protein) range from about 1.0 to about 10.0, and are most preferably about 1.44.

Pharmaceutically acceptable carriers should be inert. The carrier should not react with or otherwise reduce the effectiveness of the active ingredients, and more particularly, should not significantly diminish the effectiveness or stability of the interferon. Pharmaceutically acceptable carriers include water, ethanol, polyethylene glycol, mineral oil, petrolatum, propylene glycol, lanolin, and similar agents. Appropriate preparations for topical applications are preferably constituted in lotion, cream, oil or emulsion formulations.

The term "interferon ointment" as used herein describes an interferon antiviral preparation containing an amine stabilizing agent which has been added in an effective amount to the pharmaceutically acceptable carrier to stabilize interferon. The concentration of amine stabilizing agent added to the pharmaceutically acceptable carrier may range from about 0.1% to about 10.0% by weight, although lower or higher concentrations may be used depending on application. As stated above, formulations of 0.0001% to 0.01% are preferred in certain formulations The term "lithium interferon ointment" as used herein describes a lithium interferon antiviral preparation containing a lithium anionic stabilizing agent which has been added in an effective amount to the pharmaceutically acceptable carrier to stabilize interferon. The concentration of lithium anionic stabilizing agent added to the pharmaceutically acceptable carrier may range from about 0.1% to about 10.0% by weight, although lower or higher concentrations may be used as would be ascertainable by a person having ordinary skill in the art (such as 0.0001% to 0.01%).

The term "mixed interferon ointment" as used herein describes an interferon antiviral preparation containing a lithium anionic stabilizing agent which has been added in an effective amount to the pharmaceutically acceptable carrier to stabilize interferon, or a lithium interferon antiviral preparation containing an amine stabilizing agent which has been added in an effective amount to the pharmaceutically acceptable carrier to stabilize interferon, or mixtures thereof. The concentration of lithium anionic stabilizing agent or amine stabilizing agent added to the pharmaceutically acceptable carrier may range from about 0.1% to about 10.0% by weight, and in certain formulations is preferrably less than about 0.1% and more preferrably between about 0.0001% to 0.01%, although lower or higher concentrations may be used as would be ascertainable by a person having ordinary skill in the art.

The antiviral activity of interferon is determined by a number of methods such as those described more fully in: W. E. Stewart II, The Interferon System, Springer-Verlag (2d Ed. 1981). The Cytopathic Effect Inhibition Assay (CPE) is particularly useful for determining interferon antiviral activity. The method is described more fully in Id. at pages 17–18, which is specifically incorporated herein by reference. As used herein, the CPE method entails introducing 50 microliters of growth medium (Eagle's minimal essential medium supplemented with 5% to 10% fetal calf serum) per well into microtiter plates. Twenty-five microliters of interferon is introduced into the first well of the microtiter row and the solution mixed with a fresh micro pipette tip. A 25 microliter aliquot is transferred to the next well and mixed with a fresh micro pipette tip. Virus controls, cell controls and standards are treated similarly. The samples are exposed to sterilizing ultraviolet radiation (approximately 6 minutes at 15 centimeters with a General Electric germicidal lamp). Freshly trypsinized cell suspensions of human foreskin fibroblast cells are introduced into each well (0.1 milliliters containing about $2 \times 10^4$ cells) and the microtiter trays are incubated overnight at 37° C. A suspension of vesicular stomatitis virus (American Type Culture Collection, Camden, N.J., U.S.A.) containing about $1 \times 10^4$ plaque-forming units in 50 microliters of serum-free Eagle's minimal essential medium is introduced into each well, except cell controls, and the trays are incubated for approximately 24 hours at 37° C., at which time virus controls show 100% CPE. End-points are read microscopically as 50% protection. Residual activity thus measured is compared to the International Reference standard 6, 69/19 for human interferon (leukocyte-derived, Medical Research Council, National Institute for Biological Standards and Control, London, U.K.) tested simultaneously.

Because of the recognized inaccuracies of this biological assay (differences of less than 0.3 $\log_{10}$ cannot be objectively distinguished), all results are presented as approximate percentages of starting interferon activities. Thus, a reading of 100% activity indicates no detectible or significant loss of interferon activity. A reading of between 70 and 80% activity indicates a slight loss of interferon activity; a reading of between 30 to 60% activity indicates a significant detectible loss; a reading of between 1 to 20% activity indicates approximately a 1 to 2 $\log_{10}$ decrease in interferon activity; and a reading of 0% activity indicates no detectible activity remaining.

Another embodiment of the invention is directed to a method for making a stable interferon containing composition comprising the steps of obtaining an interferon and an other protein, which acts synergistically with interferon, to form a mixture stabilizing the mixture by adding a stabilizing agent selected from the group consisting of primary alkyl amines and chemicals which have the general formula $Li_nRX$, wherein. Li is lithium, R is an aliphatic, X is an anion, and n is a number chosen to electrochemically balance lithium with the anion, dialyzing the stable mixture to form a stable interferon comprising composition. Optionally, the composition may be lyophilized to a powder and a pharmaceutically acceptable carrier added. The interferon is selected from the group consisting of alpha, beta, gamma, omega, or recombinantly produced interferon, and the other protein, which acts synergistically with interferon, is selected from the group consisting of tumor necrosis factor, alpha, beta, gamma or omega interferon, and variants thereof. Preferably the interferon is alpha interferon and the other protein is gamma interferon.

Another embodiment of the invention is directed to medical dressings containing stabilized interferon compositions that are applied directly to the skin of a patient for the treatment of disorders of the skin and associated tissues such as common warts, plantar warts, basal cell carcinoma, squamous cell carcinoma and psoriasis. Interferon is purified by conventional means such as chromatography, recombinant engineering techniques, or another appropriate method. The purified interferon is stabilized, basically as described herein, and incorporated into a solid support such as a gel matrix which may be a polyacrylamide gel, an agarose gel, or another similar gel, resin or matrix. Alternatively, the interferon may be purified and simultaneously stabilized and incorporated into a solid support impregnated with a stabilizing agent. Incorporation is by electrophoresis, diffusion, electrostatic interaction or another appropriate method. The solid support is divided into portions, such as discs or strips, which are attached to the dressing. The dressing is attached to an affected area of the body. Examples of appropriate coverings include bandages such as self-adhesive bandages, gauze pads, and intra-dermal medical devises (implants). The interferon, being stable, remains effective for long periods of time and is slowly released by diffusion treating the affected area with minimal discomfort to the patient and without the need for continued reapplication. No harmful or irritating chemicals are present because none are required in the stabilization process. The covering remains in place on the body for extended periods of time and is easily replaced as necessary.

The following examples are offered to illustrate embodiments of the invention, but should not be viewed as limiting the scope of the invention.

EXAMPLE 1

Storage stability of interferon in stabilized interferon compositions and lithium stabilized interferon compositions was assessed. Human leukocyte interferon containing approximately 80% alpha interferon and approximately 20% omega interferon, prepared as described by Cantell, was dialyzed in physiological saline. Stabilized interferon compositions were prepared by mixing aliquots of 0.1 ml human leukocyte interferon (at $1 \times 10^4$, $1 \times 10^5$ or $1 \times 10^6$ IU/ml) with 0.9 ml physiological saline (pH 7.2) containing amine stabilizing agents at the concentrations indicated in Table 1. Lithium stabilized interferon compositions were prepared by mixing aliquots of 0.1 ml human leukocyte interferon (at $1 \times 10^4$, $1 \times 10^5$ or $1 \times 10^6$ IU/ml) with 0.9 ml physiological saline (pH 7.2) containing the lithium anionic stabilizing agents at the concentrations indicated in Table 1.

The stabilized interferon compositions and lithium stabilized interferon compositions were incubated at room temperature (20° to 24° C.) for 1 hour, 24 hours, or 1 month, and then tested for residual antiviral activity using vesicular stomatitis virus and human skin fibroblast cell lines, according to the CPE inhibition method described above. Results, expressed as percent of initial antiviral activity, are shown in Table 1.

TABLE 1

Stabilization of human interferon (20–24° C.)

| Stabilizer | Concentration of stabilizer (wt. percent) | Percent Initial Activity (storage time) | | |
|---|---|---|---|---|
| | | 1 hr | 24 hr | 1 mo. |
| Lithium octyl sulfate | 0.1 | 90 | 10 | 0 |
| | 1.0 | 100 | 70 | 10 |
| | 10.0 | 100 | 100 | 60 |
| Lithium decyl sulfate | 0.1 | 100 | 30 | 10 |
| | 1.0 | 100 | 80 | 40 |
| | 10.0 | 100 | 100 | 80 |
| Lithium dodecyl sulfate | 0.1 | 100 | 100 | 100 |
| | 1.0 | 100 | 100 | 100 |
| | 10.0 | 100 | 100 | 100 |
| Lithium tetradecyl sulfate | 0.1 | 100 | 100 | 100 |
| | 1.0 | 100 | 100 | 100 |
| Octyl amine | 0.1 | 70 | 20 | 0 |
| | 1.0 | 80 | 50 | 10 |
| | 10.0 | 100 | 70 | 10 |
| Decyl amine | 0.1 | 80 | 30 | 10 |
| | 1.0 | 80 | 50 | 10 |
| | 10.0 | 100 | 70 | 30 |
| Dodecyl amine | 0.1 | 100 | 100 | 100 |
| | 1.0 | 100 | 100 | 100 |
| | 10.0 | 100 | 100 | 100 |
| Tetradecyl amine | 0.1 | 100 | 100 | 100 |
| | 1.0 | 100 | 100 | 100 |
| Control | — | 100 | 30 | 0 |

As shown, the lithium organo sulfates are effective in stabilizing the aqueous human interferons. Most effective was lithium dodecyl sulfate and lithium tetradecyl sulfate, at concentrations ranging from 0.1 to 10% by weight. The amine stabilizing agents likewise stabilized human interferon. Most effective was dodecyl amine at concentrations of 0.1% to 10% by weight, and tetradecyl amine in concentrations of 0.1% to 1.0% by weight.

EXAMPLE 2

The stabilized interferon compositions (containing dodecyl amine at 0.1% and 1.0% by weight), prepared as described in Example 1, were stored at 37° C. for 1 hour, 24 hours, or 1 month, and tested for residual antiviral activity using the CPE inhibition assay. Unstabilized interferon in saline served as a control. Results, expressed as percent of initial antiviral activity, are shown in Table 2.

TABLE 2

Stability of Stabilized Interferon Compositions (37° C.)

| Stabilizer | Stabilizer Concentration (wt. percent) | Percent Initial Activity (storage time) | | |
|---|---|---|---|---|
| | | 1 hr | 24 hr | 1 month |
| Dodecyl amine | 0.1 | 100 | 100 | 100 |
| | 1.0 | 100 | 100 | 100 |
| Control | — | 100 | 30 | 0 |

As shown, dodecyl amine at concentrations of 0.1% and 1.0% by weight stabilized the interferon stored at 37° C.

EXAMPLE 3

The stabilized interferon compositions prepared as described in Example 1 were stored at 56° C. for 1 hour or 24 hours, and tested for residual antiviral activity as shown in Table 3. Unstabilized interferon in saline served as a control. Results are expressed as percent of initial antiviral activity.

TABLE 3

Stability of Stabilized Interferon Compositions (56° C.)

| Stabilizer | Stabilizer Concentration (wt. percent) | Percent Initial Activity (storage time) | |
|---|---|---|---|
| | | 1 hr | 24 hr |
| Dodecyl amine | 0.1 | 100 | 100 |
| | 1.0 | 100 | 100 |
| Control | — | 3 | 0 |

As shown, dodecyl amine at concentrations of 0.1% to 1.0% by weight stabilized human interferon stored for up to 24 hours.

EXAMPLE 4

Storage stability of interferon antiviral preparation was assessed. Stabilized interferon composition, prepared as in Example 2, and a control interferon in saline were each dialyzed against 0.03M ammonium bicarbonate buffer (pH 7.6) and lyophilized. The stabilized interferon composition and control interferon in powder form were each added to a pharmaceutical carrier comprising (weight percent) 10% lanolin and 90% petrolatum, and mixed at 37° C. for 1 hour. Aliquots of the interferon antiviral preparation thus obtained were stored at 4° C. for 1 month, 6 months, 12 months, and 36 months.

Following each selected storage period, aliquots of interferon antiviral preparation were mixed with equal volumes of 5% fetal calf serum-containing tissue culture medium (Eagle's minimal essential medium) and incubated for 4 hours at 37° C., and the culture medium tested for eluted residual antiviral activity by the CPE inhibition assay. The results, expressed as percent of initial antiviral activity, are shown in Table 4.

TABLE 4

Stability of interferon antiviral preparation (4° C.)

| Interferon | Percent Initial Activity (storage time) | | | |
|---|---|---|---|---|
| | 1 mo. | 6 mo. | 12 mo. | 36 mo. |
| Dodecyl amine-stabilized | 100 | 100 | 100 | 100 |
| Control | 70 | 10 | 0 | n.t.* |

*Signifies "not tested", because prior activity was already zero.

As shown, dodecyl amine treatment significantly stabilized the interferon antiviral preparation for periods of up to 36 months in samples stored at 4° C.

EXAMPLE 5

The interferon antiviral preparation in Example 4 was stored at room temperature (20°–24° C.). Results, expressed as percent of initial antiviral activity, are shown in Table 5.

TABLE 5

Stability of interferon antiviral preparation (20–24° C.)

| Interferon | Percent Initial Activity (storage time) | | | |
|---|---|---|---|---|
| | 1 mo. | 6 mo. | 12 mo. | 36 mo. |
| Dodecyl amine-stabilized | 90 | 40 | 20 | 0 |
| Control | 0 | n.t.* | n.t. | n.t. |

*Signifies "not tested", because prior activity was already zero.

As shown, dodecyl amine treatment significantly stabilized the interferon antiviral preparation for periods of at least a year in samples stored at 20°-24° C.

EXAMPLE 6

The interferon antiviral preparation in Example 4 was stored at 37° C. Results, expressed as percent of initial antiviral activity, are shown in Table 6.

TABLE 6

Stability of interferon antiviral preparation (37° C.)

| Interferon | Percent Initial Activity (storage time) | | | |
|---|---|---|---|---|
| | 1 mo. | 6 mo. | 12 mo. | 36 mo. |
| Dodecyl amine-stabilized | 50 | 20 | 0 | n.t.* |
| Control | 0 | n.t. | n.t. | n.t. |

*Signifies "not tested", because prior activity was already zero.

As shown, dodecyl amine-treatment significantly stabilized the interferon antiviral preparation for periods of up to six months in samples stored at 37° C.

EXAMPLE 7

The storage stability of interferon ointment was assessed. An interferon antiviral preparation was prepared as described in Example 4, with the exception that the pharmaceutical carrier contained 0.1% (weight percent) dodecyl amine. Aliquots of the interferon ointments thus obtained were stored at 37° C., for 1 month, 6 months, 12 months, and 36 months. Aliquots were then mixed with equal volumes of 5% fetal calf serum-containing tissue culture medium (Eagle's minimal essential medium) and incubated for 4 hours at 37° C., and the culture medium tested for eluted residual antiviral activity by the CPE inhibition assay. The results are shown in Table 7.

TABLE 7

Stability of interferon ointment (4° C.)

| Interferon | Percent Initial Activity (storage time) | | | |
|---|---|---|---|---|
| | 1 mo. | 6 mo. | 12 mo. | 36 mo. |
| Dodecyl amine-ointment | 100 | 100 | 100 | 100 |
| Control | 70 | 10 | 0 | n.t.* |

*Signifies "not tested", because prior activity was already zero.

EXAMPLE 8

The interferon ointment as in Example 7 was stored at room temperature (20°-24° C.) for 1 month, 6 months, 12 months and 36 months. Results, expressed as percent of initial antiviral activity, are shown in Table 8.

TABLE 8

Stability of interferon ointment (20-24° C.)

| Interferon | Percent Initial Activity (storage time) | | | |
|---|---|---|---|---|
| | 1 mo. | 6 mo. | 12 mo. | 36 mo. |
| Dodecyl amine-ointment | 100 | 100 | 100 | 100 |
| Control | 0 | n.t.* | n.t. | n.t. |

*Signifies "not tested", because prior activity was already zero.

EXAMPLE 9

Interferon ointments of Example 7 were stored at 37° C. for 1 month, 6 months, 12 months and 36 months. Results, expressed as percent of initial antiviral activity, are shown in Table 9.

TABLE 9

Stability of interferon ointment (37° C.)

| Interferon | Percent Initial Activity (storage time) | | | |
|---|---|---|---|---|
| | 1 mo. | 6 mo. | 12 mo. | 36 mo. |
| Dodecyl amine-ointment | 100 | 100 | 100 | 100 |
| Control | 0 | n.t.* | n.t. | n.t. |

*Signifies "not tested", because prior activity was already zero.

EXAMPLE 10

Leukocyte interferon extracted as in Example 1 was subjected to non-reducing SDS-PAGE and the alpha interferon and omega interferon fractions eluted into serum-containing medium (Eagle's minimal essential medium containing 5% fetal calf serum). Stabilized interferon compositions (1.0% by weight dodecylamine) as in Example 2 were prepared for alpha-isolate interferon and for omega-isolate interferon. Control interferon (containing both alpha and omega interferon) was prepared in saline. The stabilized interferon compositions were stored for up to one month at room temperature (20°-24° C.). Results are expressed as percent of initial antiviral activity.

TABLE 10

Stabilization of stabilized interferon compositions: Alpha and omega interferon isolates (20°-24° C.)

| Interferon | Percent Initial Activity (storage time) | | |
|---|---|---|---|
| | 1 hr | 24 hrs | 1 month |
| Alpha-isolates | 100 | 100 | 100 |
| Omega-isolates | 100 | 100 | 100 |
| Control | 100 | 30 | 0 |

EXAMPLE 11

Stabilized interferon compositions comprising alpha isolate or omega isolate, as in Example 10, were stored for up to one month at 37° C. Results are expressed as percent of initial antiviral activity.

TABLE 11

Stabilization of stabilized interferon compositions: Alpha and omega isolates (37° C.)

| Interferon | Percent Initial Activity (storage time) | | |
|---|---|---|---|
| | 1 hr | 24 hrs | 1 month |
| Alpha-isolates | 100 | 100 | 100 |
| Omega-isolates | 100 | 100 | 100 |
| Control | 100 | 30 | 0 |

EXAMPLE 12

Interferon ointments prepared as in Example 7 comprising alpha isolate or omega isolate (isolates prepared as in Example 10) were stored for up to 6 months at room temperature (20°-24° C.). Results are expressed as percent of initial antiviral activity.

TABLE 12

Stability of interferon ointment:
Alpha and omega isolates (20°–24° C.)

| Interferon | Percent Initial Activity (storage time) | |
|---|---|---|
| | 1 month | 6 months |
| Alpha-isolates | 100 | 100 |
| Omega-isolates | 100 | 100 |
| Control | 0 | n.t.* |

*Signifies "not tested", because prior activity was already zero.

EXAMPLE 13

Interferon ointments prepared as in Example 7 comprising alpha isolate or omega isolate (isolates prepared as in Example 10) were stored for up to 6 months at 37° C. Results are expressed as percent of initial antiviral activity.

TABLE 13

Stability of interferon ointment:
Alpha and omega isolates (37° C.)

| Interferon | Percent Initial Activity (storage time) | |
|---|---|---|
| | 1 month | 6 months |
| Alpha-isolates | 100 | 100 |
| Omega-isolates | 100 | 100 |
| Control | 0 | n.t.* |

*Signifies "not tested", because prior activity was already zero.

EXAMPLE 14

Interferon preparations containing lithium dodecyl sulfate, lithium tetradecyl sulfate, a dodecyl amine, or a tetradecyl amine, demonstrated 100% stability at 20°–24° C. for one month (Table 1). Further, an interferon ointment containing a dodecyl amine showed 100% stability even after 3 years at 4° C., 20°–24° C. or 37° C. (Tables 7–9). Tests have shown that when interferon compositions of the claimed invention are supplemented with mercaptoethanol and urea, nearly all activity is lost.

| Stabilizing Agent* | Inactivation Treatment | Activity Remaining |
|---|---|---|
| None | 100° C. for 2½ minutes | <10% |
| Lithium Dodecylsulfate | None | 100% |
| Lithium Dodecylsulfate | 100° C. for 2½ minutes | 100% |
| Lithium dodecylsulfate, mercaptoethanol, and urea | None | 10% |
| Lithium dodecylsulfate, mercaptoethanol, and urea | 100° C. for 2½ minutes | 10% |
| dodecyl amine | None | 100% |
| dodecyl amine | 100° C. for 2½ minutes | 100% |
| dodecyl amine, mercaptoethanol, and urea | None | 10% |
| dodecyl amine, mercaptoethanol, and urea | 100° C. for 2½ minutes | 10% |

(*)Human interferon-alpha preparations were constituted at the following reagent concentrations: lithium dodecylsulfate (1.0%), mercaptoethanol (1.0%), urea (5 M), and dodecyl amine (1.0%).

Lithium dodecyl sulfate and dodecyl amine alone each completely stabilized human interferon preparations treated for 2½ minutes at 100° C. to simulate long term storage. Activity was drastically reduced when these compositions were further supplemented with mercaptoethanol and urea indicating that such compositions are unable to effectively stabilize interferon and further, that these additional substances impair the stability and activity of the claimed composition. These experiments were repeated with compositions stored for up to one month at room temperature with nearly identical results.

EXAMPLE 15

Human interferon-alpha preparations were purified to approximately $10^6$, $10^7$ and $10^8$ units per milligram protein. Aliquots were constituted to contain 0.1, by weight, lithium dodecyl sulfate. These lithium-stabilized interferons and control interferons at each purification level in saline were each dialyzed against 0.03M ammonium bicarbonate buffer (pH 7.6) at 4° C. and lyophilized. The stabilized interferon and control interferon in powder form were added to a pharmaceutical carrier comprising (weight percent) 10% lanolin and 90 petrolatum, to a final concentration of approximately $10^5$ units/gram and mixed at 37° C. for one hour. Aliquots of the interferon antiviral preparations thus obtained were stored at 4° C. for one month and six months.

TABLE 15

STABILITY OF LITHIUM-STABILIZED INTERFERON ANTIVIRAL PREPARATIONS[1]

| Interferon Preparation | Lithium Stabilizing Agent Added | Percent Initial Activity On Storage at 4° C. for | |
|---|---|---|---|
| | | 1 Month | 6 Months |
| ~$10^6$ units/mg | +[2] | 100 | 100 |
| | – | 70 | 10 |
| ~$10^7$ units/mg | +[3] | 100 | 100 |
| | – | 70 | 3 |
| ~$10^8$ units/mg | +[4] | 100 | 100 |
| | – | 50 | 3 |

(1) Following each storage period, aliquots of interferon antiviral preparations were mixed with equal volumes of 5% fetal calfserum-containing tissue culture medium (Eagle's minimal essential medium) and incubated for four hours at 37° C., and the culture medium tested for eluted residual antiviral activity.
(2) Final lithium dodecyl sulfate concentration (weight percent) ≈ 0.01% of ointment.
(3) Final lithium dodecyl sulfate concentration (weight percent) ≈ 0.001% of ointment.
(4) Final lithium Dodecyl sulfate concentration (weight percent) ≈ 0.0001% of ointment.

The data in Table 15 illustrates that detergent-concentrations as low as 0.0001% of ointment weight afford stability to interferon topical formulations. Such low concentrations of detergent could prove useful for topical applications for stabilized-interferon ointment formulations for treating virus infections of the eye such as herpes keratitis, epidemic adenovirus-keratitis and conjunctivitis, or conjunctival papillomatosis, where higher detergent concentrations would be irritating to the eyes.

EXAMPLE 16

Amine or lithium stabilized interferon is sufficiently stable to be incorporated into a solid support and directly applied to affected areas of the body. This is accomplished by electrophoresis of purified interferon into a gel comprised of the stabilizing agent. Portions of the gel are sliced into, for example discs, and fixed to gauze patches. The gauze patches are applied directly to the affected area of the body by means of a bandage or similar device, where it can remain for long periods of time. The stable interferon leaches out of the gauze in a timed-release fashion, is not irritating because irritating chemicals are not employed. In addition, the solid support provides a protective cover from possible spread of viral particles to other areas.

Other embodiments and uses of the invention will be apparent to those skilled in the art from consideration of the specification and practice of the invention disclosed therein. It is intended that the specification and examples be considered exemplary only, with the true scope and spirit of the invention being indicated by the following claims.

I claim:

1. A composition comprising a therapeutically effective amount of an interferon which is an alpha interferon, an omega interferon, or a recombinantly produced interferon, and a stabilizing agent at less than about 0.1% by weight which is a primary alkyl amine, wherein the composition is free of agents for disrupting non-covalent bonds and agents for reducing disulfide bonds.

2. The composition of claim 1 which is a powder.

3. The composition of claim 1 wherein the powder is mixed with a pharmaceutically acceptable carrier.

4. The composition of claim 1 wherein the pharmaceutically acceptable carrier is petrolatum or lanolin.

5. The composition of claim 1 with an interferon activity of between about $10^4$ to about $10^8$ international units per milliliter.

6. The composition of claim 1 wherein the stabilizing agent comprises between about 0.0001% to about 0.01% by weight of the composition.

7. The composition of claim 1 wherein the weight ratio of the stabilizing agent to the interferon is between about 1.00 to about 1.44.

8. The composition of claim 1 wherein the primary alkyl amine is an octyl amine, a decyl amine, a dodecyl amine, or a tetradecyl amine.

9. A composition comprising a therapeutically effective amount of an interferon which is an alpha interferon, an omega interferon, or a recombinantly produced interferon, and a stabilizing agent at less than about 0.1% by weight which has the formula $Li_nRX$, wherein Li is lithium, R is an aliphatic group, X is an anion, and n is a number chosen to electrochemically balance lithium with the anion, and wherein the composition is free of agents for disrupting non-covalent bonds and agents for reducing disulfide bonds.

10. The composition of claim 9 which is a powder.

11. The composition of claim 9 wherein the powder is mixed with a pharmaceutically acceptable carrier.

12. The composition of claim 9 wherein the pharmaceutically acceptable carrier is petrolatum or lanolin.

13. The composition of claim 9 with an interferon activity of between about $10^4$ to about $10^8$ international units per milliliter.

14. The composition of claim 9 wherein the stabilizing agent comprises between about 0.0001% to about 0.01% by weight of the composition.

15. The composition of claim 9 wherein the weight ratio of the stabilizing agent to the interferon is between about 1.00 to about 1.44.

16. The composition of claim 9 wherein the stabilizing agent is a lithium octyl sulfate, a lithium decyl sulfate, a lithium dodecyl sulfate, or a lithium tetradecyl sulfate.

17. A method for making a stable interferon composition wherein the composition is free of agents for disrupting non-covalent bonds and agents for reducing disulfide bonds comprising the steps of:
   a. obtaining an interferon which is an alpha interferon, an omega interferon, or a recombinantly produced interferon,
   b. mixing the obtained interferon with less than about 0.1% by weight of a stabilizing agent which is a primary alkyl amine to form the composition, and
   c. dialyzing the composition.

18. The method of claim 17, wherein after dialysis of the composition, substantially all of the stabilizing agent is bound to the interferon and there is little free stabilizing agent present in the composition.

19. The method of claim 17 further comprising the step of lyophilizing the dialyzed composition to a powder.

20. The method of claim 19 wherein the powder is mixed with a pharmaceutically acceptable carrier.

21. The method of claim 20 wherein the pharmaceutically acceptable carrier is petrolatum or lanolin.

22. The method of claim 17 wherein the composition has an interferon activity of between about $10^4$ to about $10^8$ international units per milliliter.

23. The method of claim 17 wherein the stabilizing agent comprises between about 0.0001% to about 0.01% by weight of the composition.

24. The method of claim 17 wherein the weight ratio of the stabilizing agent to the interferon is between about 1.00 to about 1.44.

25. The method of claim 17 wherein the primary alkyl amine is an octyl amine, a decyl amine, a dodecyl amine, or a tetradecyl amine.

26. A composition made by the method of claim 17.

27. A method for making a stable interferon composition wherein the composition is free of agents for disrupting non-covalent bonds and agents for reducing disulfide bonds comprising the steps of:
   a. obtaining an amount of interferon which is an alpha interferon, an omega interferon, or a recombinantly produced interferon,
   b. mixing the obtained interferon with less than about 0.1% by weight of a stabilizing agent which has the formula $Li_nRX$, wherein Li is lithium, R is an aliphatic group, X is an anion, and n is a number chosen to electrochemically balance lithium with the anion to form the composition, and
   c. dialyzing the composition.

28. The method of claim 27, wherein after dialysis of the composition, substantially all of the stabilizing agent is bound to the interferon and there is little free stabilizing agent present in the composition.

29. The method of claim 27 further comprising the step of lyophilizing the dialyzed composition to a powder.

30. The method of claim 29 wherein the powder is mixed with a pharmaceutically acceptable carrier.

31. The method of claim 30 wherein the pharmaceutically acceptable carrier is petrolatum or lanolin.

32. The method of claim 27 wherein the composition has an interferon activity of between about $10^4$ to about $10^8$ international units per milliliter.

33. The method of claim 27 wherein the stabilizing agent comprises between about 0.0001% to about 0.01% by weight of the composition.

34. The method of claim 27 wherein the weight ratio of the stabilizing agent to the interferon is between about 1.00 to about 1.44.

35. The method of claim 27 wherein the stabilizing agent is a lithium octyl sulfate, a lithium decyl sulfate, a lithium dodecyl sulfate, or a lithium tetradecyl sulfate.

36. A composition made by the method of claim 27.

37. A method for making a stable interferon containing composition comprising the steps of:

A. mixing two proteins, one of which is an interferon and an other protein which acts synergistically with interferon, selected from the group consisting of alpha, beta, gamma, omega and recombinantly produced interferon, tumor necrosis factor and variants these proteins, to form a mixture;

B. stabilizing the mixture by adding a stabilizing agent at less than about 0.1% by weight selected from the group consisting of primary alkyl amines and chemicals which have the general formula $Li_nRX$, wherein Li is lithium, R is an aliphatic group, X is an anion, and n is a number chosen to electrochemically balance lithium with the anion, C. dialyzing the stable mixture to form a stable interferon comprising composition.

38. The method of claim 37 wherein the dialyzed mixture is lyophilized to a powder.

39. The method of claim 38 wherein a pharmaceutically acceptable carrier is added to the powder.

40. A stable interferon containing composition made by the method of claim 37.

* * * * *